US012597494B2

(12) United States Patent
Bian

(10) Patent No.: US 12,597,494 B2
(45) Date of Patent: Apr. 7, 2026

(54) METHOD AND APPARATUS FOR TRAINING MEDICAL IMAGE REPORT GENERATION MODEL, AND IMAGE REPORT GENERATION METHOD AND APPARATUS

(71) Applicant: TENCENT TECHNOLOGY (SHENZHEN) COMPANY LIMITED, Shenzhen (CN)

(72) Inventor: Cheng Bian, Shenzhen (CN)

(73) Assignee: TENCENT TECHNOLOGY (SHENZHEN) COMPANY LIMITED, Shenzhen (CN)

( * ) Notice: Subject to any disclaimer, the term of this patent is extended or adjusted under 35 U.S.C. 154(b) by 702 days.

(21) Appl. No.: 18/073,290

(22) Filed: Dec. 1, 2022

(65) Prior Publication Data

US 2023/0092027 A1     Mar. 23, 2023

Related U.S. Application Data

(63) Continuation of application No. PCT/CN2022/081537, filed on Mar. 17, 2022.

(30) Foreign Application Priority Data

Mar. 25, 2021    (CN) ......................... 202110320701.3

(51) Int. Cl.
*G16H 10/60*          (2018.01)
*G06T 7/00*           (2017.01)
*G16H 30/40*          (2018.01)

(52) U.S. Cl.
CPC ........... *G16H 10/60* (2018.01); *G06T 7/0012* (2013.01); *G16H 30/40* (2018.01); *G06T 2207/20081* (2013.01)

(58) Field of Classification Search
CPC ........ G16H 30/40; G16H 15/00; G16H 10/60; G16H 30/20; G16H 70/60; G06T 7/0012;
(Continued)

(56) References Cited

U.S. PATENT DOCUMENTS

| | | | | |
|---|---|---|---|---|
| 10,706,545 B2 * | 7/2020 | Laserson | ................ | G06N 3/044 |
| 2017/0337329 A1 * | 11/2017 | Liu | ......................... | A61B 6/463 |
| 2020/0043600 A1 * | 2/2020 | Glottmann | ............. | G16H 15/00 |

FOREIGN PATENT DOCUMENTS

| | | |
|---|---|---|
| CN | 109545302 A | 3/2019 |
| CN | 109741806 A | 5/2019 |

(Continued)

OTHER PUBLICATIONS

Yuan, Jianbo, et al. "Automatic radiology report generation based on multi-view image fusion and medical concept enrichment." International conference on medical image computing and computer-assisted intervention. Cham: Springer International Publishing (Year: 2019).*

(Continued)

*Primary Examiner* — Courtney Joan Nelson
(74) *Attorney, Agent, or Firm* — Anova Law Group, PLLC

(57)        ABSTRACT

A method for training a medical image report generation model that includes a visual feature extraction network, an encoding network, and a decoding network. The method includes: acquiring a sample medical image; extracting visual feature information of on a sample medical image through the visual feature extraction network, to obtain a visual feature sequence; concatenating a self-learning label based on the visual feature sequence, to obtain input information about the encoding network; encoding the input information through the encoding network, to obtain a visual encoding feature vector and an output task result; decoding the visual encoding feature vector through the decoding (Continued)

network, to obtain an output image report; and calculating a loss of the model based on the output image report and the output task result, and adjusting a parameter of the medical image report generation model according to the total loss function value.

20 Claims, 10 Drawing Sheets

(58) Field of Classification Search
CPC . G06T 2207/20081; G06T 2207/20084; G06T 2207/30004; G06T 5/60; G06T 2210/41; G06V 2201/03; G06V 10/82; G06V 30/19173; G06V 10/806; G06V 30/19147; G06V 30/413; G06N 3/045; G06N 20/00; G06N 3/08; A61B 6/5217; A61B 6/5205; A61B 5/7267; A61B 8/5207; A61B 6/5211; A61B 5/7264; A61B 5/0013
See application file for complete search history.

(56) References Cited

FOREIGN PATENT DOCUMENTS

| CN | 110111864 | A | 8/2019 |
| CN | 112164446 | A | 1/2021 |
| CN | 112992308 | A | 6/2021 |
| EP | 3753025 | A1 | 12/2020 |

OTHER PUBLICATIONS

Y. Wen et al., "Symptom and Pathology Report Generation for Ophthalmic Diseases in Fundus Images," 2020 IEEE International Conference on Bioinformatics and Biomedicine (BIBM), Seoul, Korea (South), 2020, pp. 349-356, doi: 10.1109/BIBM49941.2020.9313481. (Year: 2020).*

Jing, Baoyu, Pengtao Xie, and Eric Xing. "On the automatic generation of medical imaging reports." arXiv preprint arXiv:1711.08195 (2017) (Year: 2017).*

T. K. K. Ho and J. Gwak, "Utilizing Knowledge Distillation in Deep Learning for Classification of Chest X-Ray Abnormalities," in IEEE Access, vol. 8, pp. 160749-160761, 2020, doi: 10.1109/ACCESS.2020.3020802 (Year: 2020).*

Zhang, Shuai, et al. "Automated Radiological Report Generation For Chest X-Rays With Weakly-Supervised End-to-End Deep Learning." arXiv preprint arXiv:2006.10347 (2020). (Year: 2006).*

The World Intellectual Property Organization (WIPO) International Search Report for PCT/CN2022/081537 May 12, 2022 8 Pages (including translation).

Zhao Tong., "Research and Application of Automatic Generation of Medical Imaging Report based on Multimodal Machine Learning", Mar. 15, 2021, pp. 16-22 and pp. 25-27. China Master's Theses Full-text Database Master Medical and Health.

* cited by examiner

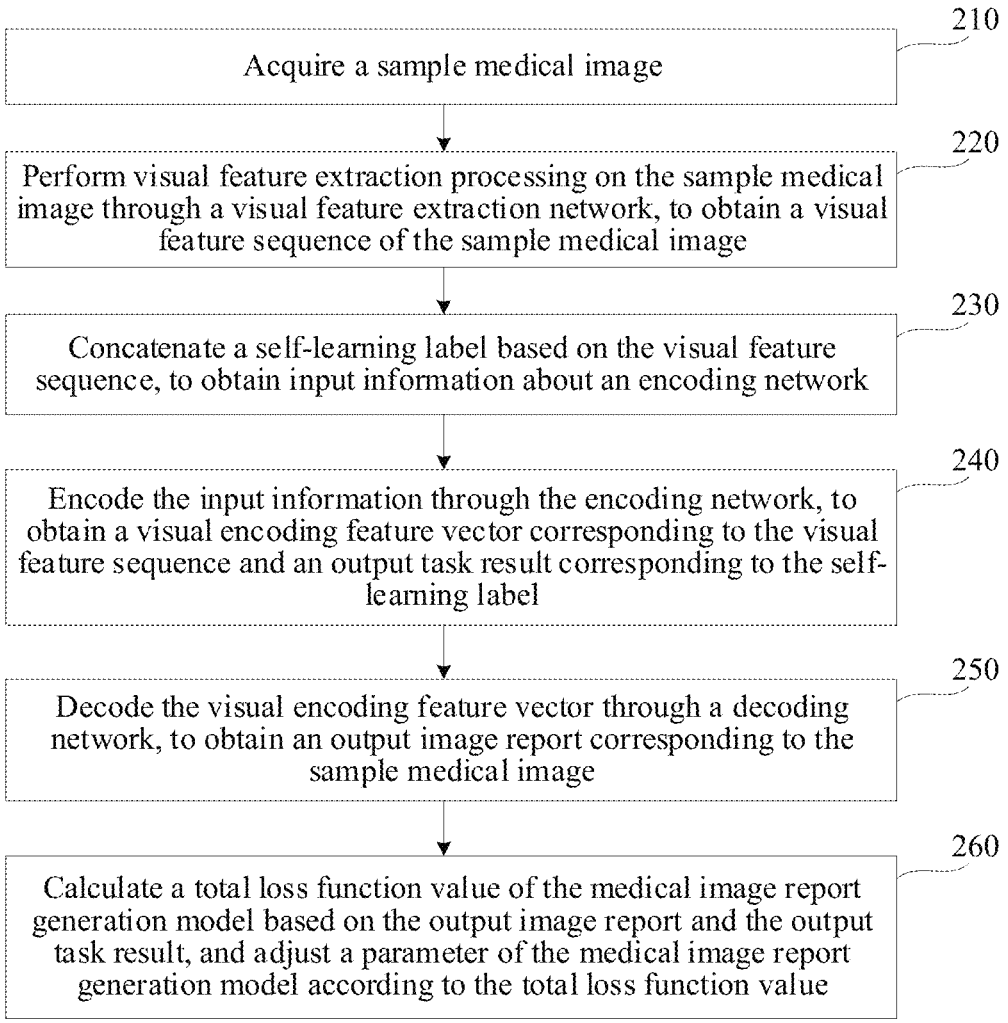

210

Acquire a sample medical image

220

Perform visual feature extraction processing on the sample medical image through a visual feature extraction network, to obtain a visual feature sequence of the sample medical image

230

Concatenate a self-learning label based on the visual feature sequence, to obtain input information about an encoding network

240

Encode the input information through the encoding network, to obtain a visual encoding feature vector corresponding to the visual feature sequence and an output task result corresponding to the self-learning label

250

Decode the visual encoding feature vector through a decoding network, to obtain an output image report corresponding to the sample medical image

260

Calculate a total loss function value of the medical image report generation model based on the output image report and the output task result, and adjust a parameter of the medical image report generation model according to the total loss function value

FIG. 2

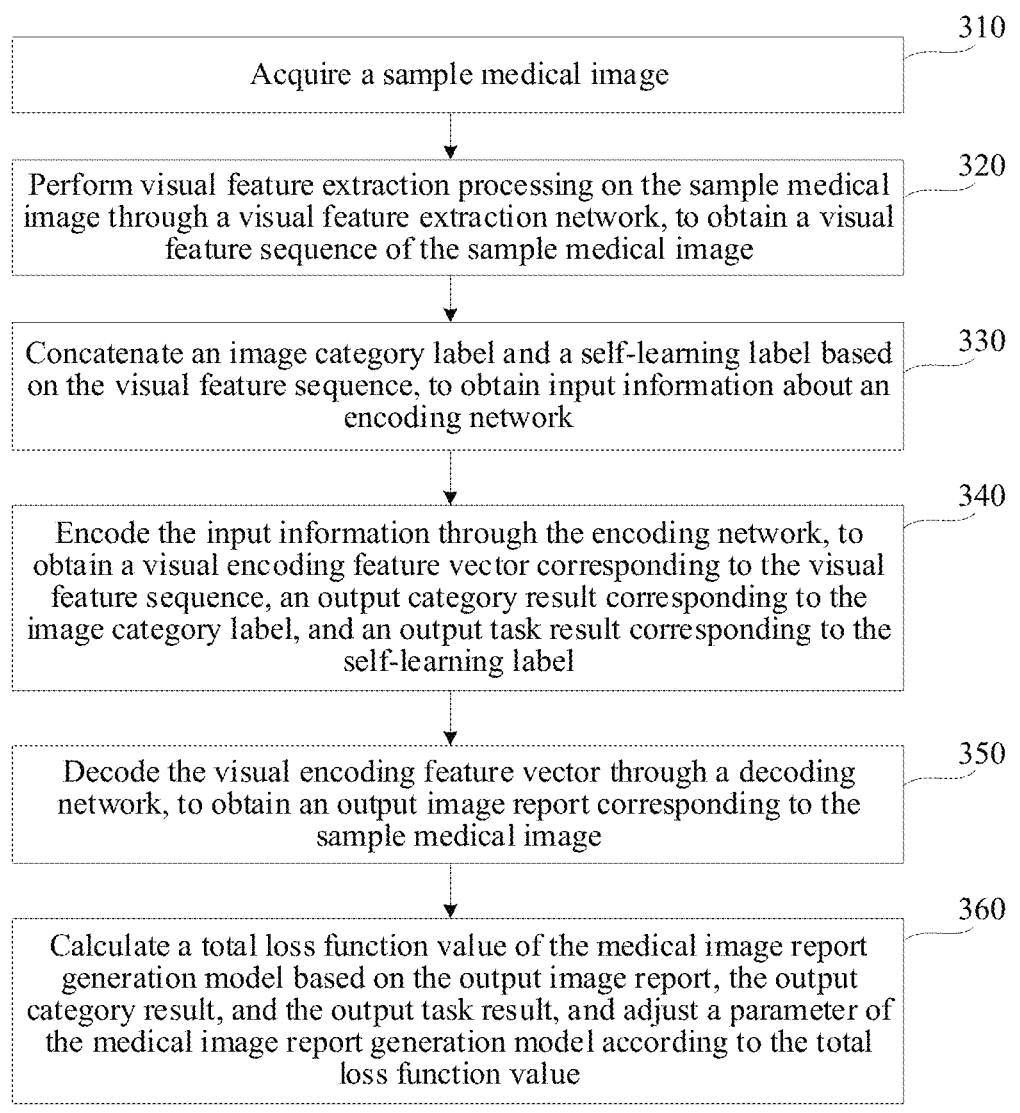

310

Acquire a sample medical image

320

Perform visual feature extraction processing on the sample medical image through a visual feature extraction network, to obtain a visual feature sequence of the sample medical image

330

Concatenate an image category label and a self-learning label based on the visual feature sequence, to obtain input information about an encoding network

340

Encode the input information through the encoding network, to obtain a visual encoding feature vector corresponding to the visual feature sequence, an output category result corresponding to the image category label, and an output task result corresponding to the self-learning label

350

Decode the visual encoding feature vector through a decoding network, to obtain an output image report corresponding to the sample medical image

360

Calculate a total loss function value of the medical image report generation model based on the output image report, the output category result, and the output task result, and adjust a parameter of the medical image report generation model according to the total loss function value

FIG. 3

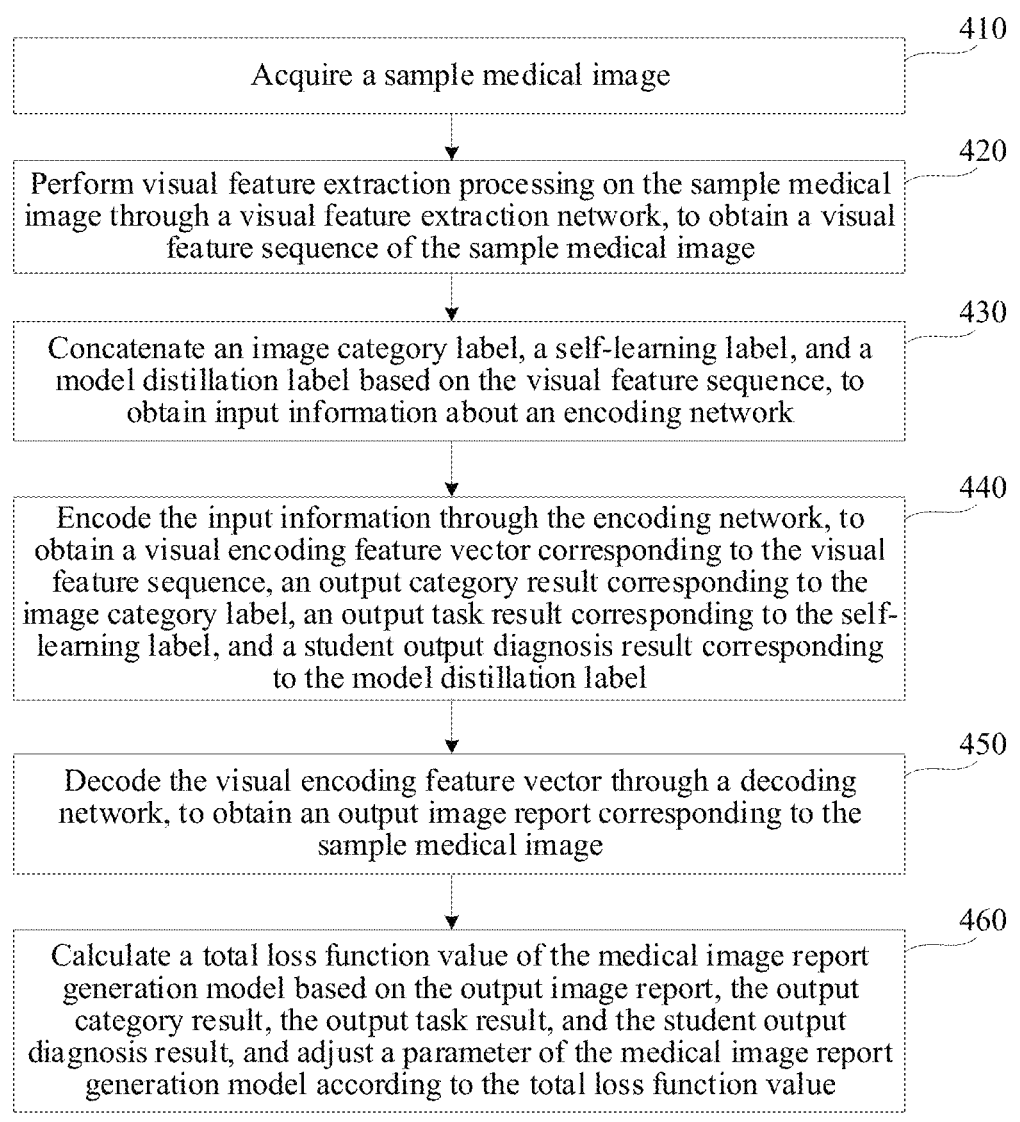

410

Acquire a sample medical image

420

Perform visual feature extraction processing on the sample medical image through a visual feature extraction network, to obtain a visual feature sequence of the sample medical image

430

Concatenate an image category label, a self-learning label, and a model distillation label based on the visual feature sequence, to obtain input information about an encoding network

440

Encode the input information through the encoding network, to obtain a visual encoding feature vector corresponding to the visual feature sequence, an output category result corresponding to the image category label, an output task result corresponding to the self-learning label, and a student output diagnosis result corresponding to the model distillation label

450

Decode the visual encoding feature vector through a decoding network, to obtain an output image report corresponding to the sample medical image

460

Calculate a total loss function value of the medical image report generation model based on the output image report, the output category result, the output task result, and the student output diagnosis result, and adjust a parameter of the medical image report generation model according to the total loss function value

FIG. 4

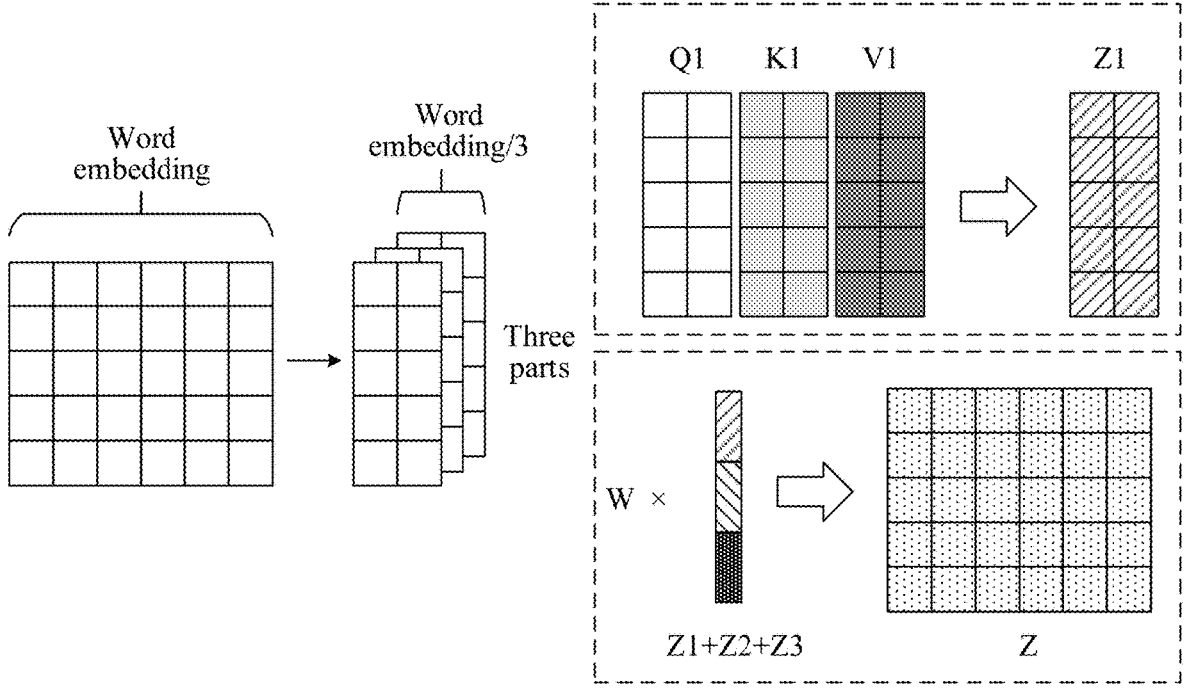
FIG. 7
$$\begin{pmatrix} 0.37 \\ 0.99 \\ 0.01 \\ 0.08 \end{pmatrix} + \boxed{\begin{array}{c} \text{Positional} \\ \text{encoding} \\ \text{(PE)} \end{array}} \rightarrow \begin{pmatrix} 0.42 \\ 0.84 \\ 0.12 \\ 0.81 \end{pmatrix}$$
FIG. 8
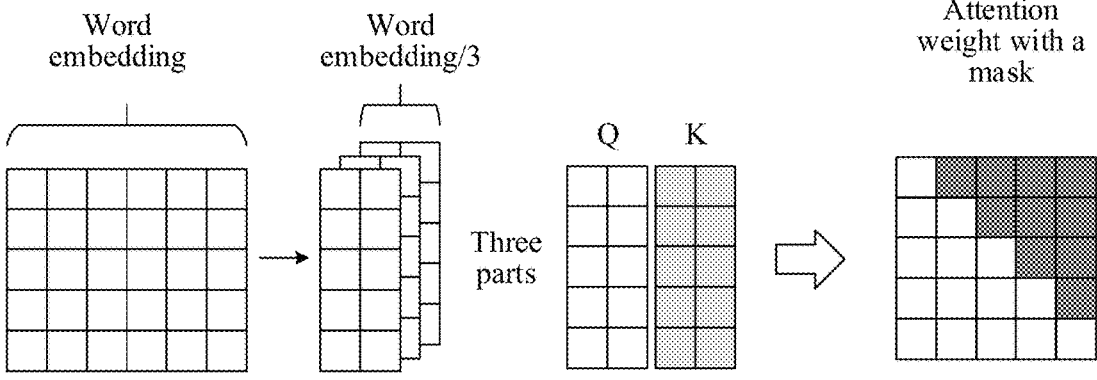
FIG. 9

Attention vector $Attention(Q,K,V) = \mathrm{soft\,max}\left(\dfrac{QK^T}{\sqrt{d_k}}\right)V$

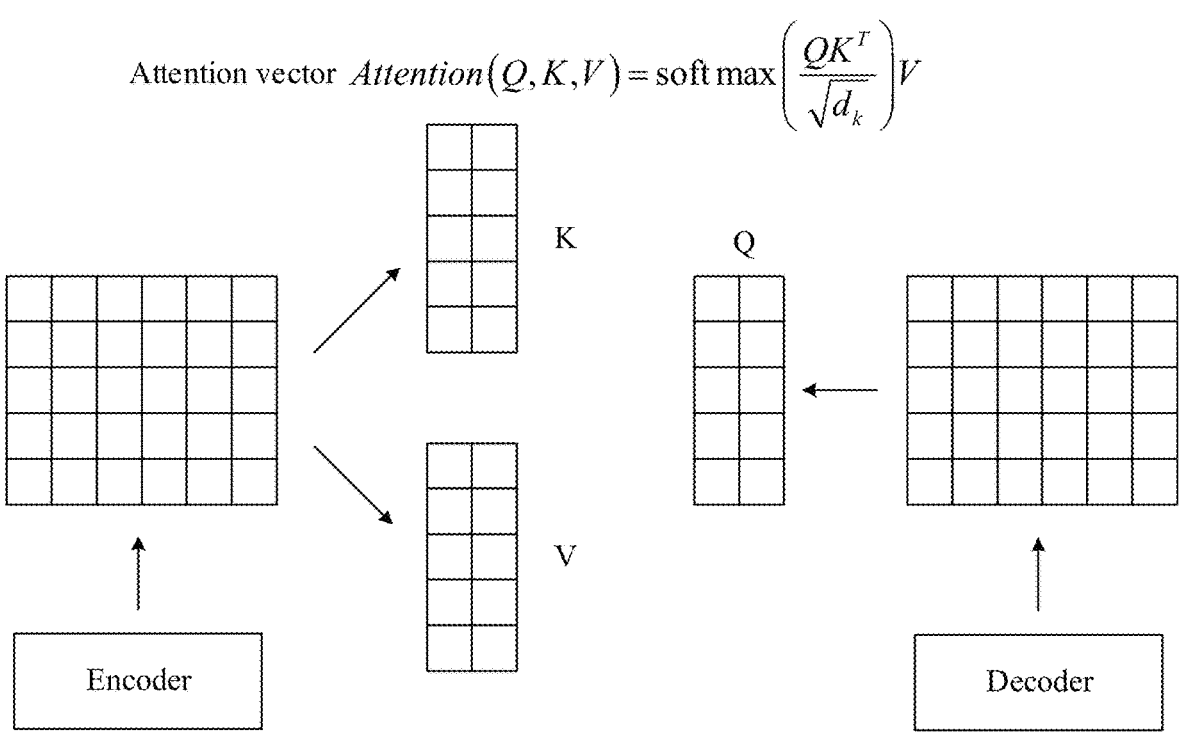

FIG. 10

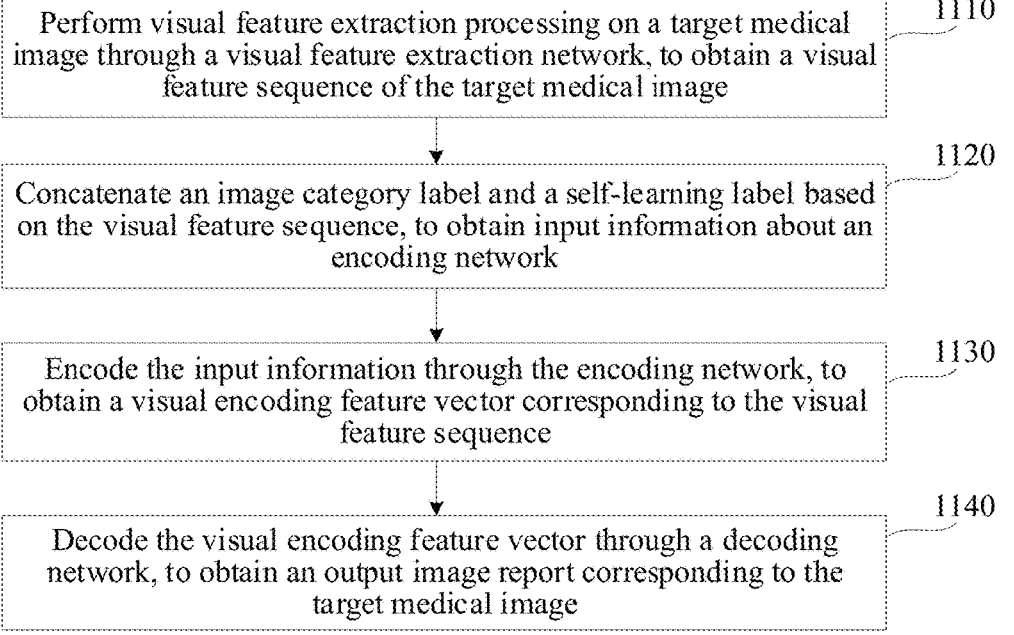

1110 — Perform visual feature extraction processing on a target medical image through a visual feature extraction network, to obtain a visual feature sequence of the target medical image 1120 — Concatenate an image category label and a self-learning label based on the visual feature sequence, to obtain input information about an encoding network 1130 — Encode the input information through the encoding network, to obtain a visual encoding feature vector corresponding to the visual feature sequence 1140 — Decode the visual encoding feature vector through a decoding network, to obtain an output image report corresponding to the target medical image

FIG. 11

METHOD AND APPARATUS FOR TRAINING MEDICAL IMAGE REPORT GENERATION MODEL, AND IMAGE REPORT GENERATION METHOD AND APPARATUS

CROSS-REFERENCES TO RELATED APPLICATIONS

This application is a continuation application of PCT Patent Application No. PCT/CN2022/081537, filed on Mar. 17, 2022, which claims priority to Chinese Patent Application No. 202110320701.3, entitled "METHOD FOR TRAINING MEDICAL IMAGE REPORT GENERATION MODEL AND IMAGE REPORT GENERATION METHOD" and filed on Mar. 25, 2021, the entire contents of both of which are incorporated herein by reference.

FIELD OF THE TECHNOLOGY

Embodiments of the present disclosure relates to the field of artificial intelligence technologies, and in particular, to a method for training a medical image report generation model and an image report generation method.

BACKGROUND OF THE DISCLOSURE

A medical image refers to an image of internal tissue of a human body or a part of the human body obtained in a non-invasive manner.

Currently, a medical image is still viewed in a manual manner clinically, and a corresponding medical image is then written. This manner may cause relatively low generation efficiency of the image report, and for a junior doctor, a problem of inaccurate report writing is prone to occur.

SUMMARY

Embodiments of the present disclosure provide a method for training a medical image report generation model and an image report generation method, to automatically generate a medical image report with high accuracy. The technical solutions are as follows: According to an aspect of the embodiments of the present disclosure, a method for training a medical image report generation model is provided. The method is performed by a computer device, and the medical image report generation model includes a visual feature extraction network, an encoding network, and a decoding network. The method includes: acquiring a sample medical image; extracting visual feature information of the sample medical image through the visual feature extraction network, to obtain a visual feature sequence of the sample medical image; concatenating a self-learning label based on the visual feature sequence, to obtain input information about the encoding network; encoding the input information through the encoding network, to obtain a visual encoding feature vector corresponding to the visual feature sequence and an output task result corresponding to the self-learning label; decoding the visual encoding feature vector through the decoding network, to obtain an output image report corresponding to the sample medical image; and calculating a total loss function value of the medical image report generation model based on the output image report and the output task result, and adjusting a parameter of the medical image report generation model according to the total loss function value.

According to an aspect of the embodiments of the present disclosure, an image report generation method based on a medical image report generation model is provided. The method is performed by a computer device, and the medical image report generation model includes a visual feature extraction network, an encoding network, and a decoding network. The method includes: extracting visual feature information of a target medical image through the visual feature extraction network, to obtain a visual feature sequence of the target medical image;

concatenating a self-learning label based on the visual feature sequence, to obtain input information about the encoding network; encoding the input information through the encoding network, to obtain a visual encoding feature vector corresponding to the visual feature sequence; and decoding the visual encoding feature vector through the decoding network, to obtain an output image report corresponding to the target medical image.

According to an aspect of the embodiments of the present disclosure, a training apparatus for a medical image report generation model is provided. The medical image report generation model includes a visual feature extraction network, an encoding network, and a decoding network, and the apparatus includes: a sample acquisition module, configured to acquire a sample medical image; a feature extraction module, configured to perform visual feature extraction processing on the sample medical image through the visual feature extraction network, to obtain a visual feature sequence of the sample medical image; an information concatenating module, configured to concatenate self-learning labels based on the visual feature sequence, to obtain input information about the encoding network; an encoding processing module, configured to encode the input information through the encoding network, to obtain a visual encoding feature vector corresponding to the visual feature sequence and an output task result corresponding to the self-learning label; a decoding processing module, configured to decode the visual encoding feature vector through the decoding network, to obtain an output image report corresponding to the sample medical image; a loss calculation module, configured to calculate a total loss function value of the medical image report generation model based on the output image report and the output task result; and a model parameter adjustment module, configured to adjust a parameter of the medical image report generation model according to the total loss function value.

According to an aspect of the embodiments of the present disclosure, an image report generation apparatus based on a medical image report generation model is provided. The medical image report generation model includes a visual feature extraction network, an encoding network, and a decoding network, and the apparatus includes: a feature extraction module, configured to perform feature extraction processing on a target medical image through the visual feature extraction network, to obtain a visual feature sequence of the target medical image; an information concatenating module, configured to concatenate self-learning labels based on the visual feature sequence, to obtain input information about the encoding network; an encoding processing module, configured to encode the input information through the encoding network, to obtain a visual encoding feature vector corresponding to the visual feature sequence; and a decoding processing module, configured to decode the visual encoding feature vector through the decoding network, to obtain an output image report corresponding to the target medical image.

According to an aspect of the embodiments of the present disclosure, a computer device is provided, the computer device including a processor and a memory, the memory storing at least one instruction, at least one program, a code set, or an instruction set, the at least one instruction, the at least one program, the code set, or the instruction set being loaded and executed by the processor to implement the foregoing method for training a medical image report generation model, or the foregoing image report generation method based on a medical image report generation model.

According to an aspect of the embodiments of the present disclosure, a non-transitory computer-readable storage medium is provided, the storage medium storing at least one instruction, at least one program, a code set, or an instruction set, the at least one instruction, the at least one program, the code set, or the instruction set being loaded and executed by a processor to implement the foregoing method for training a medical image report generation model, or the foregoing image report generation method based on a medical image report generation model.

The technical solutions provided in the embodiments of the present disclosure may include at least the following beneficial effects:

The present disclosure provides a technical solution for automatically generating a medical image report based on an artificial intelligence (AI) model. During model training, in addition to allowing the model to complete a main task (that is, to generate an image report), the model is also allowed to complete other tasks (for example, a task result) in parallel. The task result refers to an output result of a task related to self-supervised training. By introducing a self-supervised training method, an intra-class difference can further be enlarged, a feature extraction capability of a network for an inputted image can be increased, and robustness of a model network for different images and a recognition capability of the model network for an image can be improved, thereby indirectly enhancing image-to-text conversion performance of the model, and enabling the model to output a more accurate and reliable medical image report.

BRIEF DESCRIPTION OF THE DRAWINGS

FIG. 2 is a flowchart of a method for training a medical image report generation model according to an embodiment of the present disclosure.

FIG. 3 is a flowchart of a method for training a medical image report generation model according to another embodiment of the present disclosure.

FIG. 4 is a flowchart of a method for training a medical image report generation model according to another embodiment of the present disclosure.

FIG. 7 is a schematic diagram of a multi-head attention mechanism according to an embodiment of the present disclosure.

FIG. 8 is a schematic diagram of positional encoding according to an embodiment of the present disclosure.

FIG. 9 is a schematic diagram of a multi-head attention mechanism with a mask according to an embodiment of the present disclosure.

FIG. 10 is a schematic diagram of a calculation process of an attention vector according to an embodiment of the present disclosure.

FIG. 11 is a flowchart of an image report generation method according to some embodiments of the present disclosure.

DESCRIPTION OF EMBODIMENTS

The technical solutions provided in the embodiments of the present disclosure relate to technologies such as machine learning and computer vision of artificial intelligence, and are specifically described by using the following embodiments.

Figure 1:
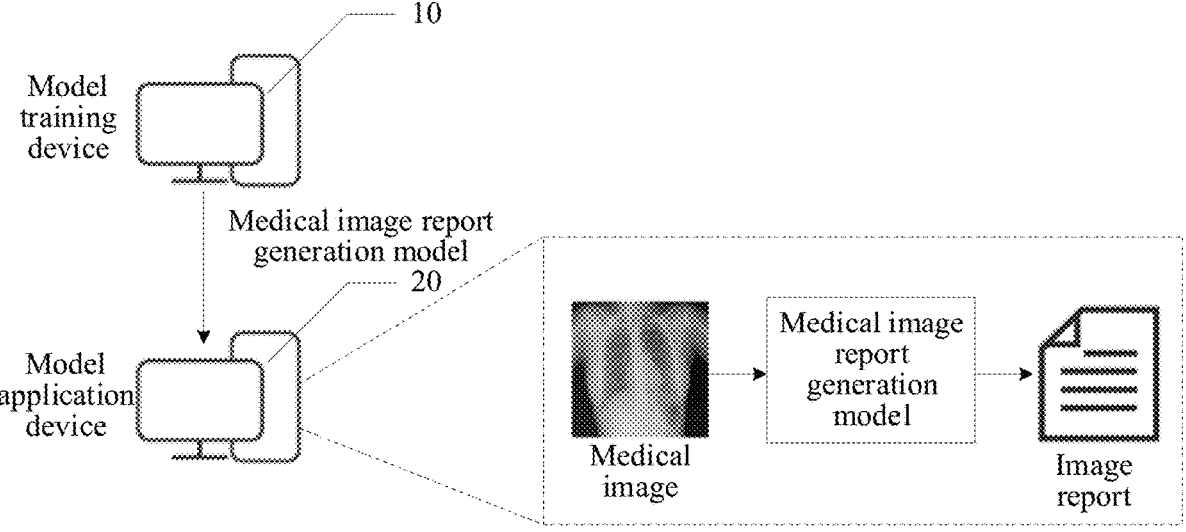
FIG. 1 is a schematic diagram of an implementation environment of a solution according to an embodiment of the present disclosure.

FIG. 1 shows a schematic diagram of an implementation environment of a solution according to an embodiment of the present disclosure. The implementation environment of the solution may include a model training device 10 and a model application device 20.

The model training device 10 may be a computer device such as a computer, a server, and the like, and is configured to train a medical image report generation model. In this embodiment of the present disclosure, the medical image report generation model is a machine learning model configured to automatically generate a corresponding image report based on a medical image. The model training device 10 may train the medical image report generation model in a machine learning manner, so that the medical image report generation model has better performance in automatically generating a medical image report.

The trained medical image report generation model may be deployed in the model application device 20 for use. The model application device 20 may be a terminal device such as a mobile phone, a tablet computer, a personal computer (PC), a smart television, a multimedia playback device, or a medical device, or may be a server. When a medical image report needs to be generated, the model application device 20 may automatically generate a medical image report through the medical image report generation model.

The medical image report generation model provided in the present disclosure can automatically generate a text report in a natural language form. The automatically generated medical image report can assist a doctor in performing illness diagnosis, and reduce a workload of the doctor, thereby helping improve generation efficiency of the medical image report.

In this embodiment of the present disclosure, the medical image report generation model includes a visual feature extraction network, an encoding network, and a decoding network. For descriptions of each network, reference may be made to the following embodiments.

In this embodiment of the present disclosure, a type of the medical image is not limited. For example, the medical image may be an X-ray image, a computed tomography (CT) image, a positron emission computed tomography (PET) image, a magnetic resonance image (MRI), a medical ultrasonic image, a medical microscope image, or the like. In addition, in this embodiment of the present disclosure, human body parts targeted by the medical image are not limited, and include but are not limited to an abdomen, an internal organ, a bone, a head, a blood vessel, and the like. Certainly, in some other embodiments, the medical image may alternatively be a medical image for an animal such as a cat and a dog, and a corresponding image report may also be automatically generated by using the technical solution of the present disclosure.

The technical solution of the present disclosure is described below by using several embodiments.

FIG. 2 shows a flowchart of a method for training a medical image report generation model according to an embodiment of the present disclosure. The execution entity of each step of the method may be the model training device 10 in the embodiment of FIG. 1, for example, a computer device such as a computer and a server. The method may include the following steps (210 to 260):

Step 210. Acquire a sample medical image.

Step 220. Perform visual feature extraction processing on the sample medical image through a visual feature extraction network, to obtain a visual feature sequence of the sample medical image.

Step 230. Concatenate a self-learning label based on the visual feature sequence, to obtain input information about an encoding network.

In this embodiment of the present disclosure, the visual feature sequence is not directly used as the input information about the encoding network, but the self-learning label is concatenated based on the visual feature sequence, to obtain the input information about the encoding network. The self-learning label is used for learning image feature information from the visual feature sequence after being processed through the encoding network, to predict a task result of the sample medical image. In some embodiments, the self-learning label are directly concatenated with the visual feature sequence to obtain the input information about the encoding network.

Step 240. Encode the input information through the encoding network, to obtain a visual encoding feature vector corresponding to the visual feature sequence and an output task result corresponding to the self-learning label.

Encoding processing is performed on the input information through the encoding network, to obtain an encoding feature vector. Two parts of information are extracted from the encoding feature vector. One part of information is used as the visual encoding feature vector corresponding to the visual feature sequence, and the other part of information is used as the output task result corresponding to the self-learning label. An output category result corresponding to the image category label refers to a category (for example, the diagnosis result described above) corresponding to the sample medical image predicted by the encoding network, and the output task result corresponding to the self-learning label refers to a task result (for example, the rotation angle described above) corresponding to the sample medical image predicted by the encoding network.

Step 250. Decode the visual encoding feature vector through a decoding network, to obtain an output image report corresponding to the sample medical image.

Step 260. Calculate a total loss function value of the medical image report generation model based on the output image report and the output task result, and adjust a parameter of the medical image report generation model according to the total loss function value.

For content of the steps of the embodiment of FIG. 2, related descriptions are given below in embodiments of FIG. 3 and FIG. 4.

Based on the above, the present disclosure provides a technical solution for automatically generating a medical image report based on an AI model. During model training, in addition to allowing the model to complete a main task (that is, to generate an image report), the model is also allowed to complete other tasks (for example, a task result) in parallel. The task result refers to an output result of a task related to self-supervised training. By introducing a self-supervised training method, an intra-class difference can further be enlarged, a feature extraction capability of a network for an inputted image can be increased, and robustness of a model network for different images and a recognition capability of the model network for an image can be improved, thereby indirectly enhancing image-to-text conversion performance of the model, and enabling the model to output a more accurate and reliable medical image report.

FIG. 3 shows a flowchart of a method for training a medical image report generation model according to another embodiment of the present disclosure. The execution entity of each step of the method may be the model training device 10 in the embodiment of FIG. 1, for example, a computer device such as a computer and a server. The method may include the following steps (310 to 360):

Step 310. Acquire a sample medical image.

The sample medical image refers to a medical image used as a training sample. The sample medical image may be selected from some known data sets. In addition, the sample medical image has a corresponding target image report, and the target image report refers to an image report that is manually generated and verified, and has a pathological description for the sample medical image.

In some embodiments, a medical image and a corresponding image report in the foregoing data sets need to meet the following requirements, so that the medical image and the corresponding image report can be used as the sample medical image and the corresponding target image report. The medical image needs to be a standardized image such as a 2D or 3D X-ray image, a CT image, a PET image, a magnetic resonance image, a medical ultrasonic image, a medical microscope image, or the like, and the image need to meet requirements for a collection region and quality. In addition, the image report corresponding to the medical image needs to be a structured report and a text-based document that is written by a qualified radiologist and that includes medical history and symptoms of a related patient, and lesions-related descriptive information and explanations included in the medical image. In some embodiments, the image report corresponding to the medical image is a structured report including the following four parts: impression, findings, comparison, and indication. In the impression part, the radiologist makes a diagnosis in conjunction with the findings part, clinical history of a patient, and guidance of imaging study. In the findings part, radiological observations of body parts detected in an imaging examination are listed. The comparison part and the indication part have little to do with the content of the present disclosure and are not described in detail.

Step 320. Perform visual feature extraction processing on the sample medical image through a visual feature extraction network, to obtain a visual feature sequence of the sample medical image.

The visual feature extraction network is a neural network for extracting a visual feature of the medical image. In some embodiments, the visual feature extraction network may be a convolutional neural network (CNN). CNN has good performance in processing a task related to the computer vision.

In an exemplary embodiment, this step includes the following sub-steps.

1. Perform visual feature extraction processing on the sample medical image through the visual feature extraction network, to obtain visual feature information about the sample medical image.

The visual feature information may be a feature map outputted after the sample medical image is processed through the visual feature extraction network. The feature map records a visual feature of the sample medical image, and includes but is not limited to image features such as a color feature, a texture feature, a shape feature, and a spatial relationship feature of the image. The color feature is a global feature that describes a surface property of a scene corresponding to an image or an image region. The texture feature is also a global feature that also describes a surface property of a scene corresponding to an image or an image region. There are two types of methods for representing the shape feature. In one type of method, the shape feature is represented as a contour feature, and in the other type of method, the shape feature is represented as a regional feature. The contour feature of the image mainly targets an outer boundary of an object, and the regional feature of the image is related to an entire shape region. The spatial relationship feature refers to mutual spatial position relationships or relative direction relationships between a plurality of objects segmented in the image. These relationships may alternatively be classified into a connection/adjacency relationship, a folding/an overlapping relationship, and an inclusion/containing relationship.

2. Divide the visual feature information into a plurality of visual feature units.

In some embodiments, block division processing is performed on the feature map corresponding to the visual feature information, to divide the feature map into a plurality of feature map sub-blocks, and each feature map sub-block corresponds to a visual feature unit. For example, the feature map corresponding to the visual feature information is divided into 5×5 feature map sub-blocks, and sizes of the feature map sub-blocks are the same.

3. Acquire a feature vector of each of the visual feature units, to obtain the visual feature sequence.

Through conversion in this step, a representation form of the visual feature information may be converted from a feature map form to a vector form. For example, the feature vector (embedding) corresponding to each visual feature unit may be obtained by multiplying each visual feature unit by a matrix W, and then the feature vectors respectively corresponding to the visual feature units are arranged in order, to obtain the visual feature sequence. The visual feature sequence is a vector sequence. In some embodiments, when the feature vector corresponding to the visual feature unit is generated, a position vector corresponding to the visual feature unit may be considered in combination. The position vector is used for representing a relative position or an absolute position of the visual feature unit in the entire visual feature information (that is, the feature map).

Step 330. Concatenate an image category label and the self-learning label based on the visual feature sequence, to obtain input information about an encoding network.

In this embodiment of the present disclosure, the visual feature sequence is not directly used as the input information about the encoding network, but the image category label and the self-learning label are concatenated based on the visual feature sequence, to obtain the input information about the encoding network. The image category label is used for learning image feature information from the visual feature sequence after being processed through the encoding network, to predict a category of the sample medical image. The self-learning label is used for learning image feature information from the visual feature sequence after being processed through the encoding network, to predict a task result of the sample medical image.

In this embodiment of the present disclosure, the category of the medical image may be classified based on the diagnosis result of the medical image. For example, different categories such as fractures, cardiac hypertrophy, pneumonia, and pulmonary edema are included. In addition to classifying the image from the perspective of the diagnosis result, the classification task herein may further classify the image from another perspective. For example, the classification task herein may be another classification task that recognizes a category of an organ included in the image and disease grading of a lesion in the image. This is not limited in the present disclosure. Through the image category label, classification may be performed based on the diagnosis result of the medical image, thereby improving the robustness of the model network for different categories of images and further enhancing the image-to-text conversion performance of the model, thereby enabling the model to output a more accurate and reliable medical image report.

In this embodiment of the present disclosure, the foregoing task result refers to an output result of a task related to the self-supervised training. In a process of training the medical image report generation model, the present disclosure introduces a self-supervised training method, which can further enlarge the intra-class difference, and improve the feature extraction capability of the network for an inputted image. The task related to the self-supervised training may be set according to a requirement. For example, the task may be to determine a rotation angle of the inputted image, for example, to determine how many 90 degrees the inputted image is rotated by. The inputted sample medical image may be randomly unrotated, or rotated by 90 degrees, 180 degrees, or 270 degrees. The rotated image is inputted into the visual feature extraction network for subsequent processing, and the corresponding task result, that is, a prediction result for the rotation angle, is outputted by the encoding network.

Step 340. Encode the input information through the encoding network, to obtain a visual encoding feature vector corresponding to the visual feature sequence, an output category result corresponding to the image category label, and an output task result corresponding to the self-learning label.

Encoding processing is performed on the input information through the encoding network, to obtain an encoding feature vector. Three parts of information are extracted from the encoding feature vector. One part of information is used as the visual encoding feature vector corresponding to the visual feature sequence, another part of information is used as the output category result corresponding to the image category label, and still another part of information is used as the output task result corresponding to the self-learning label. The output category result corresponding to the image category label refers to a category (for example, the diagnosis result described above) corresponding to the sample medical image predicted by the encoding network, and the output task result corresponding to the self-learning label refers to the task result (for example, the rotation angle described above) corresponding to the sample medical image predicted by the encoding network.

Step 350. Decode the visual encoding feature vector through a decoding network, to obtain an output image report corresponding to the sample medical image.

The visual encoding feature vector is further transmitted to the decoding network for decoding processing, and the output image report corresponding to the sample medical image is outputted by the decoding network. In this embodiment of the present disclosure, the image report outputted by the decoding network is an image report in a text form, and the image report in the text form is a report that is in a sentence/paragraph form and conforms to a natural language specification, but is not a report with some simple keywords.

Step 360. Calculate a total loss function value of the medical image report generation model based on the output image report, the output category result, and the output task result, and adjust a parameter of the medical image report generation model according to the total loss function value.

In this embodiment of the present disclosure, in addition to completing the main task (that is, generating the image report), the model has also completed other tasks (including determination of the image category and the task result) in parallel. Therefore, loss functions of the model include not only a loss function corresponding to the main task, but also loss functions corresponding to other tasks. A total loss function of the model is finally obtained by adding all loss functions together.

In some embodiments, the total loss function value of the model is calculated in the following manner:

1. Calculate a first loss function value based on the output image report and the target image report corresponding to the sample medical image.

The output image report refers to an image report outputted by the model, and is specifically an image report outputted by the decoding network. The target image report, which has been described above, refers to an image report manually written by a professional doctor. By comparing a difference between the output image report and the target image report, the performance of the model in terms of report generation can be learned. In some embodiments, a first loss function may be a cross-entropy loss used for measuring the difference between the output image report and the target image report. Therefore, by training the medical image report generation model based on the first loss function, the accuracy and the reliability of the medical image report generated by the model can be improved.

2. Calculate a second loss function value based on the output category result and a target category result corresponding to the sample medical image.

The output category result refers to a category result outputted by the model, and is specifically a category result outputted by the encoding network. The target category result refers to an accurate category result. In some embodiments, information about a designated field is extracted from the target image report corresponding to the sample medical image, and semantic recognition is performed on the designated field, to obtain the target category result corresponding to the sample medical image. For example, information about the impression part is extracted from the target image report, and semantic recognition is performed on the information in this part, to obtain a diagnosis result. The diagnosis result is used as the target category result. In this embodiment of the present disclosure, the target category result can be obtained by performing semantic recognition on the information about the designated field without analyzing the full text of the target image report, thereby reducing a time consumed by the semantic recognition, and saving processing resources of the computer device.

By comparing a difference between the output category result and the target category result, performance of the model in terms of category determination can be learned. In some embodiments, a second loss function may be a cross-entropy loss used for measuring the difference between the output category result and the target category result.

In this embodiment of the present disclosure, the target category result can be automatically extracted from the target image report corresponding to the sample medical image, thereby eliminating a need to manually annotate the target category result, and helping improve training efficiency of the model. In addition, by training the medical image report generation model based on the second loss function, accuracy of the model in performing category determination can be improved, thereby further improving the accuracy and reliability of the medical image report generated by the model.

3. Calculate a third loss function value based on the output task result and a target task result corresponding to the sample medical image.

The output task result refers to a task result outputted by the model, and is specifically a task result outputted by the encoding network. The target task result refers to an accurate task result. In some embodiments, when the task is to determine the rotation angle of the inputted image, the sample medical image after being rotated by a designated angle is inputted into the visual feature extraction network. Correspondingly, the target task result is used for indicating a real rotation angle of the sample medical image, and the output task result is used for indicating a predicted rotation angle of the sample medical image. When the inputted sample medical image may be randomly unrotated, or rotated by 90 degrees, 180 degrees, or 270 degrees, and the task is to determine how many 90 degrees the inputted image are rotated by, the task results may be represented by using 0, 1, 2, and 3, which respectively correspond to unrotated, rotated by 90 degrees, rotated by 180 degrees, and rotated by 270 degrees. For another example, when the inputted sample medical image may be randomly unrotated, or rotated by any angle (for example, 10 degrees, 36 degrees, 45 degrees, 110 degrees, 305 degrees, and the like), and the task is to determine a specific angle by which the inputted image is rotated, the task result may be represented by using an angle value, which is used for representing the rotation angle corresponding to the sample medical image. In this embodiment of the present disclosure, the rotation angle of the medical image is used as the task result, so that the model can recognize medical images of various angles, thereby reducing a probability of inaccurate image recognition caused by existence of the image rotation angle, and further improving the robustness of the model in recognizing images of different angles.

By comparing a difference between the output task result and the target task result, performance of the model in terms of task result determination can be learned. In some embodiments, a third loss function may be a cross-entropy loss used for measuring the difference between the output task result and the target task result. Therefore, by training the medical image report generation model based on the third loss function, accuracy of the model in determining the task result can be improved, thereby further improving the accuracy and reliability of the medical image report generated by the model.

In some embodiments, to reduce uncertainty introduced by the task, in addition to a cross entropy between the output task result and the target task result, the third loss function may further include an information entropy of the output task result. The formula of the third loss function $L_{St}$ may be as follows:

$$L_{St}=L_{CE}(Z_p,y_p)+\Sigma Z_p \log(Z_p)$$

$Z_p$ represents the output task result, $y_p$ represents the target task result, $L_{CE}(Z_p,y_p)$ represents the cross entropy between the output task result and the target task result, and $\Sigma Z_p \log(Z_p)$ represents the information entropy of the output task result.

4. Calculate the total loss function value based on the first loss function value, the second loss function value, and the third loss function value.

In some embodiments, weighted summation is performed on the first loss function value, the second loss function value, and the third loss function value, to obtain the total loss function value. Weights corresponding to the loss functions may be reasonably set and adjusted according to actual situations. For example, the weights may be set according to importance of tasks or may be adjusted according to a model training effect, so that importance of the loss functions is adjusted, thereby obtaining a model that focuses on particular or some performance. This is not limited in the present disclosure.

Based on the above, the present disclosure provides a technical solution for automatically generating a medical image report based on an AI model. During model training, in addition to allowing the model to complete a main task (that is, to generate an image report), the model is also allowed to complete other tasks (including determination of the image category and the task result) in parallel, which helps improve the recognition capability of the model network for an image, thereby indirectly enhancing the image-to-text conversion performance of the model, and enabling the model to output a more accurate and reliable medical image report.

In addition, the medical image report generation model is adjusted from a plurality of dimensions based on the first loss function value, the second loss function value, and the third loss function value, to enable the trained model to meet indicators of the plurality of dimensions, thereby improving the accuracy and reliability of the medical image report generated by the model.

FIG. 4 shows a flowchart of a method for training a medical image report generation model according to another embodiment of the present disclosure. The execution entity of each step of the method may be the model training device 10 in the embodiment of FIG. 1, for example, a computer device such as a computer and a server. The method may include the following steps (410 to 460):

Step 410. Acquire a sample medical image.

Step 420. Perform visual feature extraction processing on the sample medical image through a visual feature extraction network, to obtain a visual feature sequence of the sample medical image.

Step 430. Concatenate an image category label, a self-learning label, and a model distillation label based on the visual feature sequence, to obtain input information about an encoding network.

In this embodiment, the model distillation label is further added. The model distillation label is used for learning image feature information from the visual feature sequence after being processed through the encoding network, to predict a category of the sample medical image. The category herein may also be classified based on a diagnosis result of the medical image. For example, different categories such as fractures, cardiac hypertrophy, pneumonia, and pulmonary edema are included.

Step 440. Encode the input information through the encoding network, to obtain a visual encoding feature vector corresponding to the visual feature sequence, an output category result corresponding to the image category label, an output task result corresponding to the self-learning label, and a student output diagnosis result corresponding to the model distillation label.

In this embodiment, encoding processing is performed on the input information through the encoding network, to obtain an encoding feature vector. Four parts of information are extracted from the encoding feature vector. The first part of information is used as the visual encoding feature vector corresponding to the visual feature sequence, the second part of information is used as the output category result corresponding to the image category label, the third part of information is used as the output task result corresponding to the self-learning label, and the fourth part of information is used as the student output diagnosis result corresponding to the model distillation label. The output category result corresponding to the image category label refers to the category (for example, the diagnosis result described above) corresponding to the sample medical image predicted by the encoding network, the output task result corresponding to the self-learning label refers to a task result (for example, the rotation angle described above) corresponding to the sample medical image predicted by the encoding network, and the student output diagnosis result corresponding to the model distillation label refers to the diagnosis result corresponding to the sample medical image predicted by the encoding network.

Step 450. Decode the visual encoding feature vector through a decoding network, to obtain an output image report corresponding to the sample medical image.

Step 460. Calculate a total loss function value of the medical image report generation model based on the output image report, the output category result, the output task result, and the student output diagnosis result, and adjust a parameter of the medical image report generation model according to the total loss function value.

In this embodiment of the present disclosure, in addition to completing a main task (that is, generating the image report), the model has also completed other tasks (including determination of the image category, the task result, and the diagnosis result) in parallel. Therefore, loss functions of the model include not only a loss function corresponding to the main task, but also loss functions corresponding to other tasks. A total loss function of the model is finally obtained by adding all loss functions together.

In some embodiments, the total loss function value of the model is calculated in the following manner:

1. Calculate a first loss function value based on the output image report and a target image report corresponding to the sample medical image.

2. Calculate a second loss function value based on the output category result and a target category result corresponding to the sample medical image.

3. Calculate a third loss function value based on the output task result and a target task result corresponding to the sample medical image.

4. Calculate a fourth loss function value based on the student output diagnosis result and a teacher output diagnosis result corresponding to the sample medical image.

The student output diagnosis result refers to a diagnosis result outputted by the medical image report generation model, and is specifically a diagnosis result outputted by the encoding network. The teacher output diagnosis result refers to a diagnosis result outputted by a pre-trained teacher model. In some embodiments, the sample medical image is inputted into the pre-trained teacher model, which is configured to recognize a symptom category (that is, the diagnosis result) in the sample medical image; and the teacher output diagnosis result corresponding to the sample medical image is obtained through the teacher model. During training of the teacher model, the sample medical image may be used for training, and a target diagnosis result is used as label information about model training. The target diagnosis result may be a diagnosis result extracted from an impression part of the target image report corresponding to the sample medical image. After that, the pre-trained teacher model is configured to perform model distillation on the medical image report generation model, to improve accuracy of the model and simplify a structure of the model network, thereby saving storage resources occupied by the model and processing resources required during use of the model, improving operating efficiency of the model, and further improving the image recognition capability of the medical image report generation model. In addition, by using the pre-trained teacher model to perform model distillation on the medical image report generation model, a convergence speed of the medical image report generation model can be sped up during training, thereby improving training efficiency of the medical image report generation model.

By comparing a difference between the student output diagnosis result and the teacher output diagnosis result, performance of the model in terms of diagnosis result recognition can be learned. In some embodiments, a fourth loss function may be a cross-entropy loss used for measuring the difference between the student output diagnosis result and the teacher output diagnosis result.

In an example, a formula of the fourth loss function $L_{global}$ may be as follows:

$$L_{global}=(1-\lambda)L_{CE}(\psi(Z_s))+\lambda\tau^2 KL(\psi(Z_s/\tau),\psi(Z_t/\tau))$$

$Z_s$ and $Z_t$ are respectively an output of a student model (that is, the medical image report generation model) and an output put of the teacher model, that is, $Z_s$ is the student output diagnosis result, and $Z_t$ is the teacher output diagnosis result. y is the target diagnosis result, $L_{CE}(\psi(Z_s),y)$ represents a cross entropy between the student output diagnosis result and the target diagnosis result, KL represents Kullback-Leibler (KL) divergence, $\psi$ represents a softmax function, and $\lambda\tau$ are hyperparameters. For example, $\lambda$ is set to be 0.5, and $\tau$ is set to be 1.

In this embodiment of the present disclosure, the target diagnosis result can be automatically extracted from the target image report corresponding to the sample medical image, thereby eliminating a need to manually annotate the target diagnosis result, and helping improve the training efficiency of the model.

5. Calculate the total loss function value based on the first loss function value, the second loss function value, the third loss function value, and the fourth loss function value.

In some embodiments, weighted summation is performed on the first loss function value, the second loss function value, the third loss function value, and the fourth loss function value, to obtain the total loss function value.

In this embodiment, newly added content compared to the embodiment of FIG. 2 is mainly described. For a part that is not described in detail in this embodiment, reference may be made to the descriptions in the embodiment of FIG. 2, and details are not described again in this embodiment.

Based on the above, in this embodiment, the model distillation label is further introduced to allow the model to complete the diagnosis task. It is found through experiments that compared with simply using two image labels, performance of a finally obtained medical image report generation model is better by introducing the model distillation label. The reason is that the model distillation label can learn an induction hypothesis from the teacher model, which can improve an effect of the performance of the medical image report generation model.

In an exemplary embodiment, the medical image report generation model may use a model architecture of CNN+ Transformer. CNN is used as the visual feature extraction network, and Transformer includes a plurality of cascaded encoders and a plurality of cascaded decoders. The plurality of cascaded encoders are used as an encoding network, and the plurality of cascaded decoders are used as a decoding network.

Figure 5:
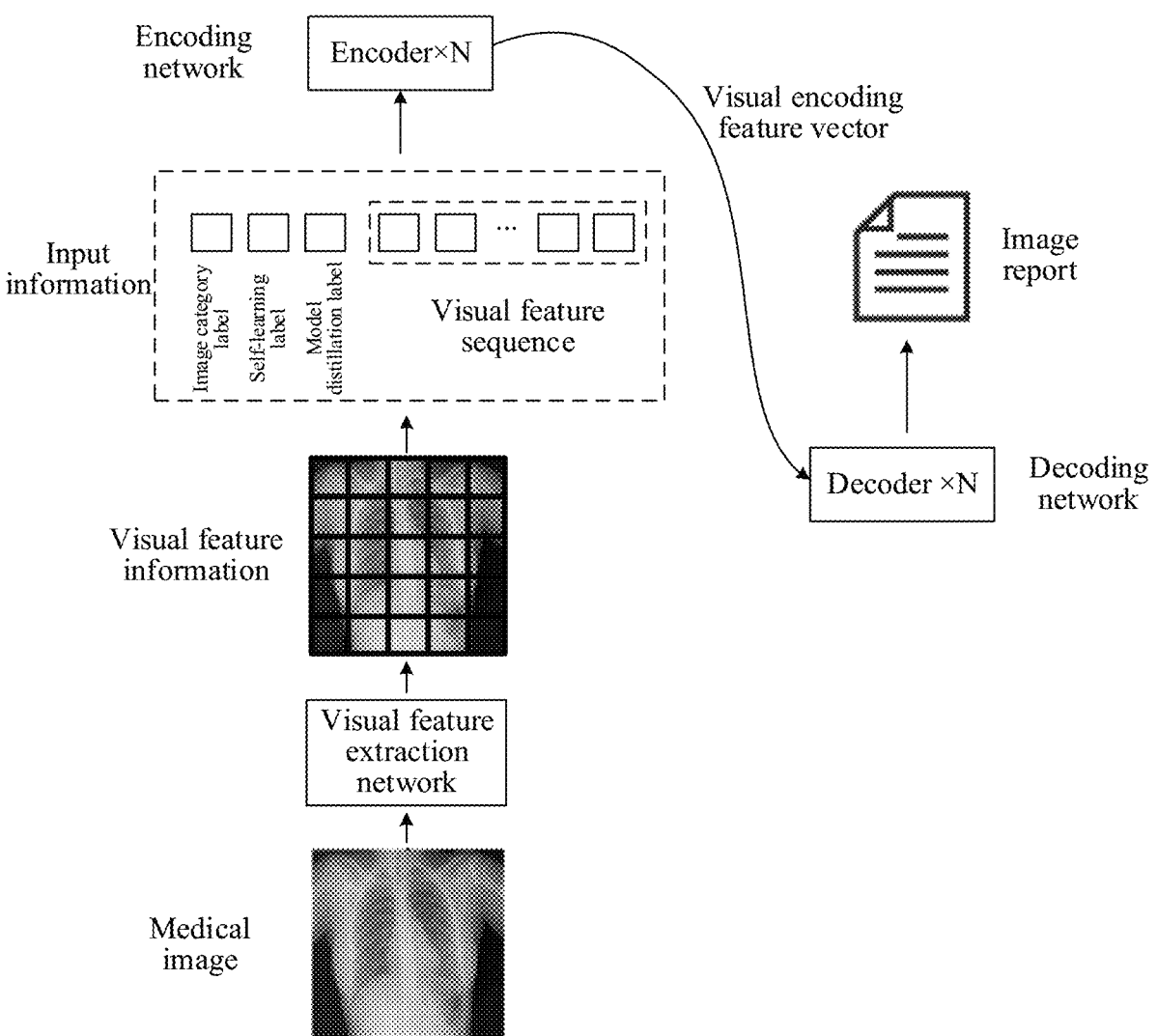
FIG. 5 is an architectural diagram of a medical image report generation model according to an embodiment of the present disclosure.

In some embodiments, FIG. 5 exemplarily shows an architecture diagram of a medical image report generation model. The model uses the model architecture of CNN+ Transformer and includes a visual feature extraction network, an encoding network, and a decoding network. The visual feature extraction network uses a CNN structure, and the encoding network and the decoding network use a Transformer structure. The encoding network includes N cascaded encoders, and the decoding network includes N cascaded decoders. N is an integer greater than 1. For example, a value of N is 6. Feature extraction processing is performed on a medical image through the visual feature extraction network, to obtain visual feature information. The visual feature information is divided into a plurality of visual feature units, and then a feature vector of each of the visual feature units is acquired, to obtain a visual feature sequence. An image category label, a self-learning label, and a model distillation label are concatenated based on the visual feature sequence, to obtain input information about the encoding network. Encoding processing is performed on the input information through the encoding network, to obtain a visual encoding feature vector corresponding to the visual feature sequence. Decoding processing is performed on the visual encoding feature vector through the decoding network, to obtain an image report corresponding to the medical image.

The encoding network and the decoding network constructed based on the Transformer structure are described below. The Transformer structure is a sequence to sequence model, and a special feature thereof is that a self-attention mechanism is widely used in the Transformer structure. A network model constructed based on the Transformer structure uses the self-attention mechanism instead of a recurrent neural network (RNN) sequence structure, which enables the model to be trained in parallel and have global information.

Figure 6:
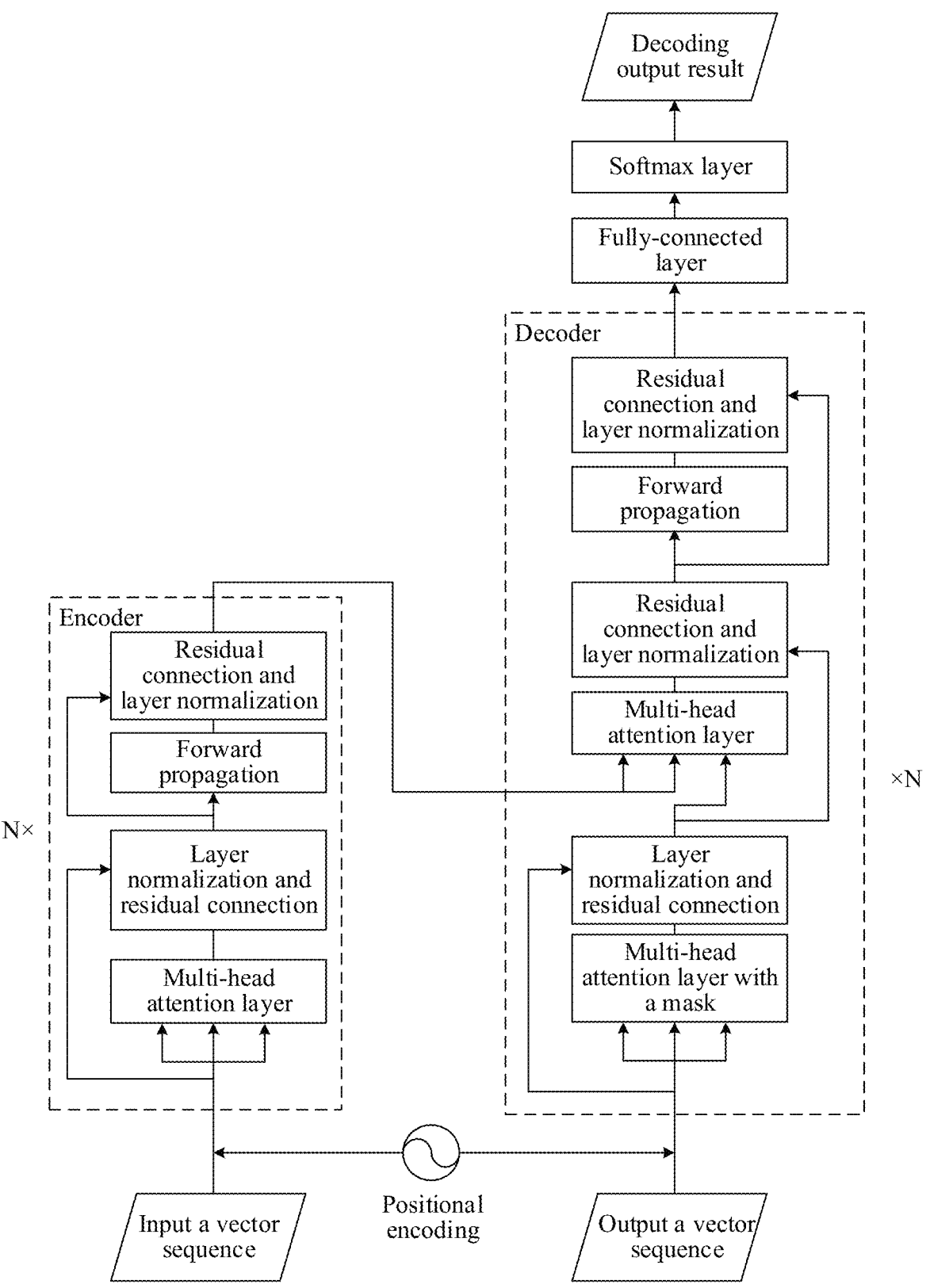
FIG. 6 is a schematic diagram of a Transformer structure according to an embodiment of the present disclosure.

FIG. 6 exemplarily shows a schematic diagram of a Transformer structure. The encoder part is on the left side, and the decoder part is on the right side. For ease of understanding, a text translation task is first used as an example to describe the Transformer structure. For the text translation task, an input is a to-be-translated word sequence, and an output is a translated word sequence.

In the encoder part, each word in the to-be-translated word sequence sequentially goes through embedded encoding, positional encoding, the multi-head attention layer, residual connection and layer normalization, forward propagation, and residual connection and layer normalization in parallel, to calculate encoded K and V vectors of each word, and then the vectors are transmitted to the decoder.

In the decoder part, a translation result (or a start tag) of a previous word is inputted, and the translation result sequentially goes through embedded encoding, positional encoding, a multi-head attention layer with a mask, and residual connection and layer normalization, to obtain a decoded Q vector. After that, K and V vectors of a current word and the decoded Q vector sequentially go through the multi-head attention layer, residual connection and layer normalization, forward propagation, residual connection and layer normalization, a fully-connected layer, and a Softmax layer, to obtain a translation result of the current word. Finally, translation results of all words are concatenated, to obtain the translated word sequence.

An example in which "machine learning" is translated into "machine learning" is used. An input at the encoder is "machine learning" (including two words "machine" and "learning"). A first input at the decoder is <BOS> (representing the start tag), and an output is "machine". An input at the decoder at a next moment is "machine", and an output is "learning". The foregoing process is continuously repeated until an end tag (for example, a period) is outputted, which indicates end of the translation. The encoder part can perform calculation in parallel, and encodes all encoder inputs once. However, the decoder part does not solve all the sequences at once, but solves the sequences one by one like a RNN does. Therefore, the decoder part needs to use a decoding output of a previous position as the Q vector of the attention mechanism.

The attention mechanism can explore relationships between words, and such relationships have been commonly used in the computer vision (CV) technology. A word embedding may be obtained in response to a given word. A query (Q) vector, a key (K) vector, and a value (V) vector corresponding to this word may be obtained through three independent fully-connected layers. K vectors of different words are dot-multiplied by the Q vector of the current word, and then dot products are multiplied by the V vector of the current word after normalization and Softmax are performed on the dot products, to obtain an attention vector of the current word to another word, thereby implementing a self-attention process. Pure self-attention always pays too much attention to the current word and weakens information about other words. Such information is actually not very useful. To resolve this problem, a multi-head attention mechanism is used.

In the multi-head attention mechanism, as shown in FIG. 7, a word embedding processed by Q, K, and V is split into h parts, and h is three herein. Through three different types of Q, K and V, different Zs (hidden layer features) are obtained. Obviously, the current Z has weakened a characteristic of focusing on itself. Then, Q, K, and V are concatenated together, and a final Z (hidden layer) vector is calculated through a fully-connected layer W. Now, the current Z may be regarded as a new feature that averages different regions of interest. In addition, such multi-head calculation has another advantage, that is, parallel calculation can be performed.

In addition, a position at which a word/feature is located is very important for sequence conversion (for example, text translation or image-to-text conversion). Therefore, after an image feature and a word embedding are obtained, position information about the word needs to encoded, and an encoding manner is shown in FIG. 8, where pos represents a position of a word in a current sentence, i represents a dimension corresponding to the word embedding, a value range of i is [0, d/2), and d is a set value such as 512. Therefore, during positional encoding (PE), each word and dimension are encoded differently. An odd number is encoded by using a sin formula, and an even number is encoded by using a cos formula. Details are as follows:

$$PE_{(pos,2i)}=\sin(pos/10000^{2i/d});$$

$$PE_{(pos,2i+1)}=\cos(pos/10000^{2i/d}).$$

Through a residual connection, a phenomenon of gradient disappearance due to deepening of modules in the Transformer can be avoided, which is used for preventing network degradation. Therefore, the Z vector and an original input X vector are added first. Then a variance and an average value of channel dimensions of current word vectors are calculated through layer normalization, and then inputted into the forward layer after normalization is performed thereon.

Finally, obtained attention results are sent to two fully-connected layers, one of which is used for dimensionality improvement and the other of which is used for dimensionality reduction. Next, residual connection and layer normalization are performed, to obtain a final output result of the encoder.

In the decoder, when a translation result is inputted into the decoder, a subsequent output cannot be seen. Therefore, a mask mechanism is forcibly added when an attention mechanism is constructed. Briefly, as shown in FIG. 9, after an attention weight (obtained by multiplying a matrix of the Q vector and a matrix of the K vector) is obtained, the attention weight is multiplied by an upper triangular matrix. Then, upper triangular regions are set to be invalid. In this case, after softmax is performed, these regions that are set to be invalid are all 0, thereby preventing information about the decoder from being let out.

A calculation manner of this module is basically the same as that of a multi-attention module. The only difference is that K and V are obtained from the encoder. As shown in FIG. 10, the attention vector may be obtained according to the following formula:

$$\text{Attention}(Q, K, V) = \text{softmax}\left(\frac{QK^T}{\sqrt{d_k}}\right)V$$

$d_k$ represents the dimension of the Q vector and the K vector.

When the Transformer structure is applied to the present disclosure to perform an image-to-text conversion task, an original medical image is converted into a visual feature sequence after feature extraction processing is performed thereon through the visual feature extraction network. Then, an image category label, a self-learning label, and a model distillation label are concatenated based on the visual feature sequence, to obtain input information about an encoding network. In this case, the input information is a vector sequence. Therefore, by performing encoding processing and decoding processing through a Transformer network, an image report in a text form can be outputted.

The foregoing embodiments describe the method for training a medical image report generation model, and the following describes an image report generation method based on the medical image report generation model by using embodiments. Content involved during use of the medical image report generation model and content involved during training of the medical image report generation model correspond to each other and are in communication with each other. Therefore, for details that are not described in one part, reference may be made to the descriptions in another part.

FIG. 11 shows a flowchart of an image report generation method according to an embodiment of the present disclosure. The execution entity of each step of the method may be the model application device 20 in the embodiment of FIG. 1, for example, a terminal device such as a mobile phone, a tablet computer, a PC, or a medical device, or a server. The method may include the following steps (1010 to 1040):

> Step 1110. Perform visual feature extraction processing on a target medical image through a visual feature extraction network, to obtain a visual feature sequence of the target medical image.

The target medical image may be any medical image. By using the method provided in this embodiment, an image report corresponding to the target medical image can be automatically generated through a medical image report generation model.

In some embodiments, visual feature extraction processing is performed on the target medical image through the visual feature extraction network, to obtain visual feature information about the target medical image; the visual feature information is divided into a plurality of visual feature units; and a feature vector of each of the visual feature units is acquired, to obtain the visual feature sequence.

> Step 1120. Concatenate an image category label and the self-learning label based on the visual feature sequence, to obtain input information about an encoding network.

In some embodiments, the image category label, the self-learning label, and a model distillation label are concatenated based on the visual feature sequence, to obtain the input information about the encoding network.

The image category label, the self-learning label, and the model distillation label concatenated herein are completely the same as the image category label, the self-learning label, and the model distillation label concatenated during model training. For example, during model training, the image category label, the self-learning label, and the model distillation label are three all-zero vectors, that is, all elements in the vectors are 0. In this case, during use of the model, the three labels are also three all-zero vectors.

> Step 1130: Encode the input information through the encoding network, to obtain a visual encoding feature vector corresponding to the visual feature sequence.

Encoding processing is performed on the input information through the encoding network, to obtain an encoding feature vector.

When the input information includes the visual feature sequence, the image category label, and the self-learning label, three parts of information are extracted from the encoding feature vector. One part of information is used as the visual encoding feature vector corresponding to the visual feature sequence, another part of information is used as an output category result corresponding to the image category label, and still another part of information is used as an output task result corresponding to the self-learning label. The output category result corresponding to the image category label refers to a category (for example, the diagnosis result described above) corresponding to the target medical image predicted by the encoding network, and the output task result corresponding to the self-learning label refers to a task result (for example, the rotation angle described above) corresponding to the target medical image predicted by the encoding network.

When the input information includes the visual feature sequence, the image category label, the self-learning label, and the model distillation label, four parts of information are extracted from the encoding feature vector. The first part of information is used as the visual encoding feature vector corresponding to the visual feature sequence, the second part of information is used as the output category result corresponding to the image category label, the third part of information is used as the output task result corresponding to the self-learning label, and the fourth part of information is used as a student output diagnosis result corresponding to the model distillation label. The output category result corresponding to the image category label refers to the category (for example, the diagnosis result described above) corresponding to the target medical image predicted by the encoding network, the output task result corresponding to the self-learning label refers to the task result (for example, the rotation angle described above) corresponding to the target medical image predicted by the encoding network, and the student output diagnosis result corresponding to the model distillation label refers to a diagnosis result corresponding to the target medical image predicted by the encoding network.

> Step 1140. Decode the visual encoding feature vector through a decoding network, to obtain an output image report corresponding to the target medical image.

The visual encoding feature vector is further transmitted to the decoding network for decoding processing, and the output image report corresponding to the target medical image is outputted by the decoding network. In this embodiment of the present disclosure, the image report outputted by the decoding network is an image report in a text form, and the image report in the text form is a report that is in a sentence/paragraph form and conforms to a natural language specification, but is not a report with some simple keywords.

In some embodiments, if required, at least one of the category result, the task result, or the diagnosis result corresponding to the target medical image outputted by the encoding network may be further acquired.

Based on the above, the present disclosure provides a technical solution for automatically generating a medical image report based on an AI model. During model training, in addition to allowing the model to complete a main task (that is, to generate an image report), the model is also allowed to complete other tasks (including determination of the image category, the task result, and the diagnosis result) in parallel, which helps improve the recognition capability of the model network for an image. Correspondingly, during use of the model, the image category label, the self-learning label, and the model distillation label are similarly concatenated based on the visual feature sequence, to obtain the input information about the encoding network, thereby enabling the model to output a more accurate and reliable medical image report.

Figure 12:
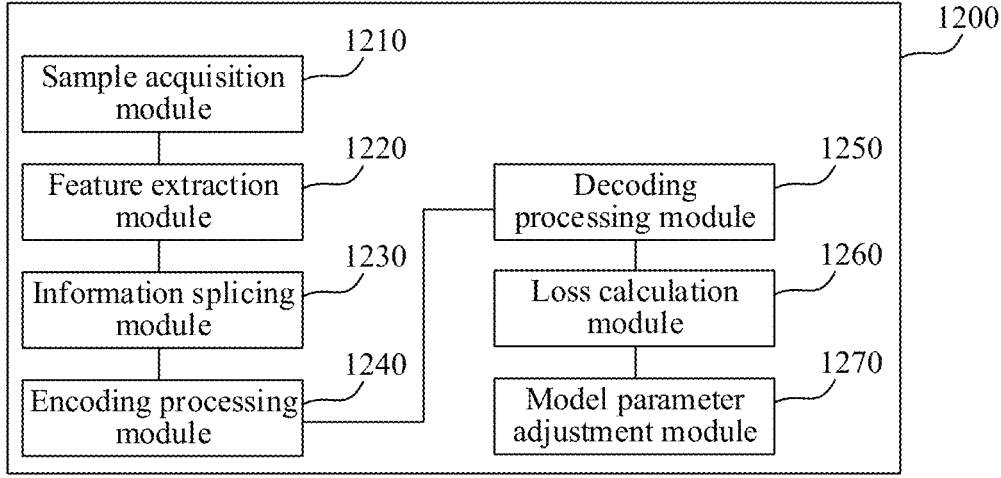
FIG. 12 is a block diagram of a training apparatus for a medical image report generation model according to an embodiment of the present disclosure.

FIG. 12 shows a block diagram of a training apparatus for a medical image report generation model according to an embodiment of the present disclosure. The apparatus has functions of implementing the foregoing method for training a medical image report generation model. The functions may be implemented by hardware, or may be implemented by hardware executing corresponding software. The apparatus may be a computer device or may be disposed in a computer device. The apparatus 1200 may include: a sample acquisition module 1210, a feature extraction module 1220, an information concatenating module 1230, an encoding processing module 1240, a decoding processing module 1250, a loss calculation module 1260, and a model parameter adjustment module 1270.

The sample acquisition module 1210 is configured to acquire a sample medical image.

The feature extraction module 1220 is configured to perform visual feature extraction processing on the sample medical image through the visual feature extraction network, to obtain a visual feature sequence of the sample medical image.

The information concatenating module 1230 is configured to concatenate a self-learning label based on the visual feature sequence, to obtain input information about the encoding network.

The encoding processing module 1240 is configured to encode the input information through the encoding network, to obtain a visual encoding feature vector corresponding to the visual feature sequence and an output task result corresponding to the self-learning label.

The decoding processing module 1250 is configured to decode the visual encoding feature vector through the decoding network, to obtain an output image report corresponding to the sample medical image.

The loss calculation module 1260 is configured to calculate a total loss function value of the medical image report generation model based on the output image report and the output task result.

The model parameter adjustment module 1270 is configured to adjust a parameter of the medical image report generation model according to the total loss function value.

In an exemplary embodiment, the loss calculation module 1260 is configured to:

calculate a first loss function value based on the output image report and a target image report corresponding to the sample medical image;

calculate a third loss function value based on the output task result and a target task result corresponding to the sample medical image; and calculate the total loss function value based on the first loss function value and the third loss function value.

In an exemplary embodiment, the feature extraction module 1220 is configured to:

inputting the sample medical image after being rotated by a designated angle into the visual feature extraction network, wherein the target task result is used for indicating a real rotation angle of the sample medical image, and the output task result is used for indicating a predicted rotation angle of the sample medical image.

In an exemplary embodiment, the input information further includes a model distillation label, and the model distillation label is processed through the encoding network, to obtain a student output diagnosis result.

The loss calculation module 1260 is further configured to:

calculate a fourth loss function value based on the student output diagnosis result and a teacher output diagnosis result corresponding to the sample medical image; and calculate the total loss function value based on the first loss function value, the third loss function value, and the fourth loss function value.

In an exemplary embodiment, the sample acquisition module 1210 is further configured to:

inputting the sample medical image into a pre-trained teacher model, the teacher model being configured to recognize a symptom category in the sample medical image; and obtain the teacher output diagnosis result corresponding to the sample medical image through the teacher model.

In an exemplary embodiment, the loss calculation module 1260 is further configured to:

perform weighted summation on the first loss function value, the third loss function value, and the fourth loss function value, to obtain the total loss function value.

In an exemplary embodiment, the input information further includes an image category label The image category label is processed through the encoding network, to obtain an output category result corresponding to the image category label.

The loss calculation module 1260 is further configured to:

calculate a second loss function value based on the output category result and a target category result corresponding to the sample medical image; and calculate the total loss function value based on the first loss function value, the second loss function value, and the third loss function value.

In an exemplary embodiment, the sample acquisition module 1210 is further configured to:

extracting information about a designated field from the target image report corresponding to the sample medical image; and perform semantic recognition on the information about the designated field, to obtain the target category result corresponding to the sample medical image.

In an exemplary embodiment, the feature extraction module 1220 is configured to:

performing visual feature extraction processing on the sample medical image through the visual feature extraction network, to obtain visual feature information about the sample medical image;

divide the visual feature information into a plurality of visual feature units; and acquiring a feature vector of each of the visual feature units, to obtain the visual feature sequence.

Based on the above, the present disclosure provides a technical solution for automatically generating a medical image report based on an AI model. During model training, in addition to allowing the model to complete a main task (that is, to generate an image report), the model is also allowed to complete other tasks (for example, a task result) in parallel. The task result refers to an output result of a task related to self-supervised training. By introducing a self-supervised training method, an intra-class difference can further be enlarged, a feature extraction capability of a network for an inputted image can be increased, and robustness of a model network for different images and a recognition capability of the model network for an image can be improved, thereby indirectly enhancing image-to-text conversion performance of the model, and enabling the model to output a more accurate and reliable medical image report.

Figure 13:
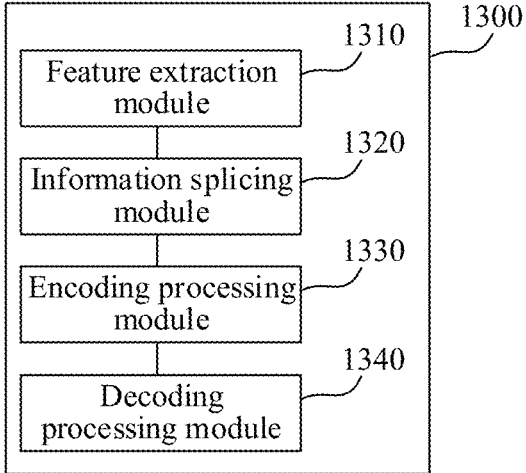
FIG. 13 is a block diagram of an image report generation apparatus according to an embodiment of the present disclosure.

FIG. 13 shows a block diagram of an image report generation apparatus according to an embodiment of the present disclosure. The apparatus has functions of implementing the foregoing image report generation method. The functions may be implemented by hardware, or may be implemented by hardware executing corresponding software. The apparatus may be a computer device or may be disposed in a computer device. The apparatus 1300 may include: a feature extraction module 1310, an information concatenating module 1320, an encoding processing module 1330, and a decoding processing module 1340.

The feature extraction module 1310 is configured to perform feature extraction processing on a target medical image through the visual feature extraction network, to obtain a visual feature sequence of the target medical image.

The information concatenating module 1320 is configured to concatenate a self-learning label based on the visual feature sequence, to obtain input information about the encoding network.

The encoding processing module 1330 is configured to encode the input information through the encoding network, to obtain a visual encoding feature vector corresponding to the visual feature sequence.

The decoding processing module 1340 is configured to decode the visual encoding feature vector through the decoding network, to obtain an output image report corresponding to the target medical image.

In an exemplary embodiment, the information concatenating module 1320 is configured to concatenate an image category label and the self-learning label based on the visual feature sequence, to obtain the input information about the encoding network.

In an exemplary embodiment, the information concatenating module 1320 is configured to:

concatenating the image category label, the self-learning label, and a model distillation label based on the visual feature sequence, to obtain the input information about the encoding network.

In an exemplary embodiment, the feature extraction module 1310 is configured to:

performing visual feature extraction processing on the target medical image through the visual feature extraction network, to obtain visual feature information about the target medical image;

divide the visual feature information into a plurality of visual feature units; and acquiring a feature vector of each of the visual feature units, to obtain the visual feature sequence.

Based on the above, the present disclosure provides a technical solution for automatically generating a medical image report based on an AI model. During model training, in addition to allowing the model to complete a main task (that is, to generate an image report), the model is also allowed to complete other tasks (including determination of the image category, the task result, and the diagnosis result) in parallel, which helps improve the recognition capability of the model network for an image. Correspondingly, during use of the model, the image category label, the self-learning label, and the model distillation label are similarly concatenated based on the visual feature sequence, to obtain the input information about the encoding network, thereby enabling the model to output a more accurate and reliable medical image report.

Figure 14:
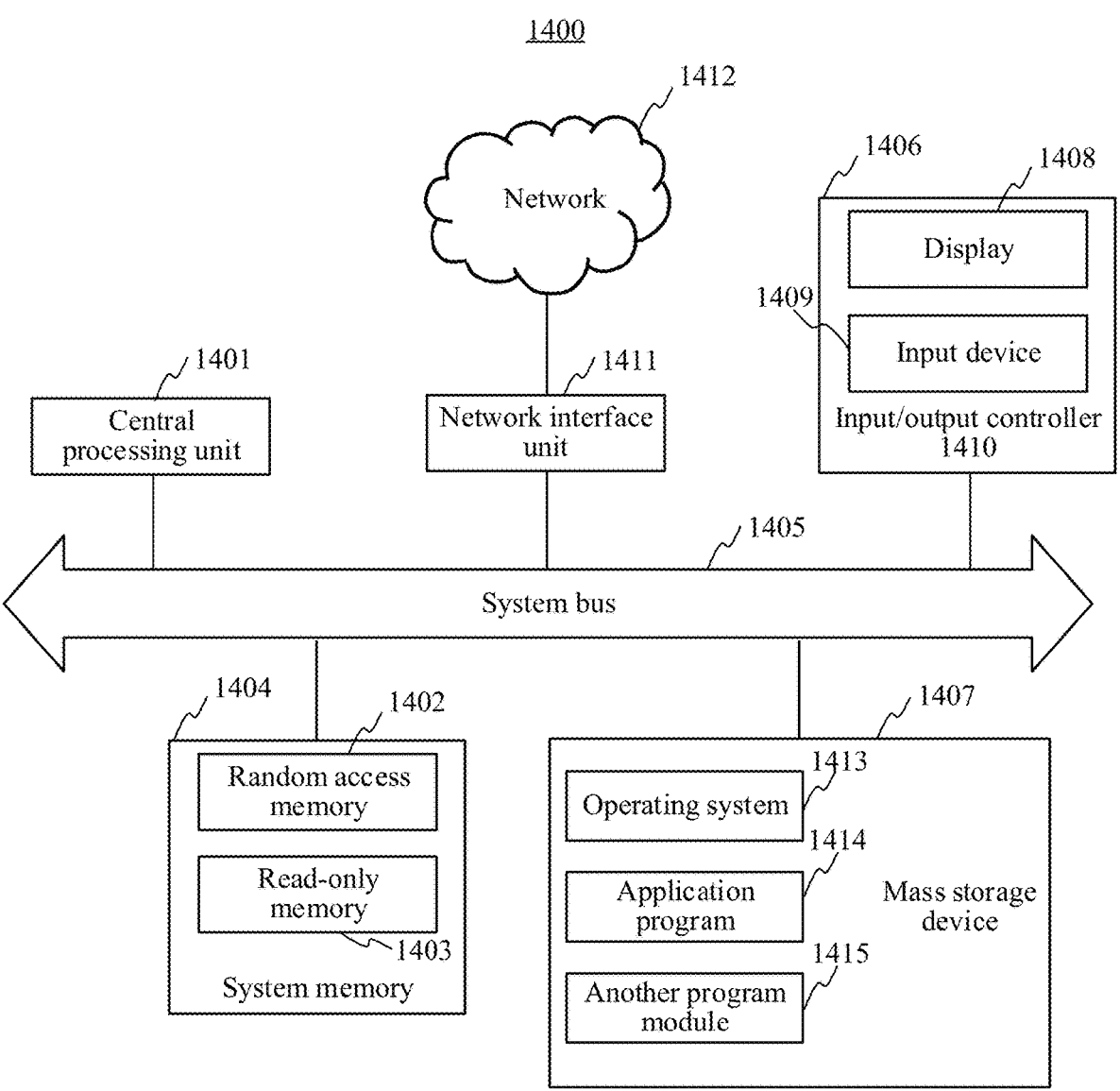
FIG. 14 is a schematic structural diagram of a computer device according to an embodiment of the present disclosure.

FIG. 14 is a schematic structural diagram of a computer device according to an embodiment of the present disclosure. The computer device may be any electronic device with a data computing function, a data processing function, and a data storage function, for example, a mobile phone, a tablet computer, a personal computer (PC), a server, or the like. The computer device is configured to perform the method for training a medical image report generation model or the image report generation method provided in the foregoing embodiments. Specifically, the computer device 1400 includes a central processing unit 1401 (such as a central processing unit (CPU), a graphics processing unit (GPU), and a field programmable gate array (FPGA)), a system memory 1404 including a random-access memory 1402 (RAM) and a read-only memory 1403, and a system bus 1405 connecting the system memory 1404 and the central processing unit 1401. The computer device 1400 further includes a basic input/output system (I/O system) 1406 configured to transmit information between components in the server, and a mass storage device 1407 configured to store an operating system 1414, an application program 1414, and another program module 1415.

The basic I/O system 1406 includes a display 1408 configured to display information, and an input device 1409 used by a user to input information, such as a mouse or a keyboard. The display 1408 and the input device 1409 are both connected to the CPU 1401 by using an input/output controller 1410 connected to the system bus 1405. The basic I/O system 1406 may further include the I/O controller 1410 configured to receive and process inputs from a plurality of other devices such as a keyboard, a mouse, or an electronic stylus. Similarly, the input/output controller 1410 further provides output to a display screen, a printer, or other types of output devices.

The large-capacity storage device 1407 is connected to the CPU 1401 by using a large-capacity storage controller (not shown) connected to the system bus 1405. The mass storage device 1407 and an associated computer-readable medium provide non-volatile storage for the computer device 1400. That is, the mass storage device 1407 may include a computer-readable medium (not shown) such as a hard disk or a compact disc read-only memory (CD-ROM) drive.

Without loss of generality, the computer-readable medium may comprise a computer storage medium and a communication medium. The computer storage medium comprises volatile and non-volatile, removable and non-removable media that are configured to store information such as computer-readable instructions, data structures, program modules, or other data and that are implemented by using any method or technology. The computer storage medium includes a RAM, a ROM, an erasable programmable ROM (EPROM), an electrically erasable programmable ROM (EEPROM), a flash memory or another solid-state memory technology, a CD-ROM, a digital versatile disc (DVD) or another optical memory, a tape cartridge, a magnetic cassette, a magnetic disk memory, or another magnetic storage device. Certainly, a person skilled in the art can know that the computer storage medium is not limited to the foregoing several types. The system memory 1404 and the mass storage device 1407 may be collectively referred to as a memory.

According to the embodiments of the present disclosure, the computer device 1400 may further be connected, through a network such as the Internet, to a remote computer on the network. That is, the computer device 1400 may be connected to a network 1412 by using a network interface unit 1411 connected to the system bus 1405, or may be connected to another type of network or a remote computer system (not shown) by using a network interface unit 1411.

The memory further includes at least one instruction, at least one program, a code set, or an instruction set. The at least one instruction, the at least one program, the code set, or the instruction set is stored in the memory and is configured to be executed by one or more processors to implement the foregoing method for training a medical image report generation model or the image report generation method.

In an exemplary embodiment, a computer-readable storage medium is further provided, the storage medium storing at least one instruction, at least one program, a code set or an instruction set, and the at least one instruction, the at least one program, the code set or the instruction set being executed by the processor of a computer device to implement the foregoing method for training a medical image report generation model or the image report generation method.

In some embodiments, the computer-readable storage medium may include: a read-only memory (ROM), a random access memory (RAM), a solid state drive (SSD), an optical disc, or the like. The RAM may include a resistance random access memory (ReRAM) and a dynamic random access memory (DRAM).

In an exemplary embodiment, a computer program product or a computer program is provided. The computer program product or the computer program includes computer instructions, and the computer instructions are stored in a computer-readable storage medium. A processor of the computer device reads the computer instructions from the computer-readable storage medium, and the processor executes the computer instructions, to cause the computer device to perform the foregoing method for training a medical image report generation model or the image report generation method.

"A plurality of" mentioned in the specification means two or more. The present disclosure is not limited to the accurate structures that are described above and that are shown in the accompanying drawings, and modifications and changes may be made without departing from the scope of the present disclosure. The scope of the present disclosure is limited by the appended claims only.

What is claimed is:

1. A method for training a medical image report generation model, performed by a computer device, the medical image report generation model comprising a visual feature extraction network, an encoding network, and a decoding network, the method comprising:

acquiring a sample medical image;

extracting visual feature information of the sample medical image through the visual feature extraction network, to obtain a visual feature sequence of the sample medical image;

concatenating a self-learning label based on the visual feature sequence, to obtain input information about the encoding network;

encoding the input information through the encoding network, to obtain a visual encoding feature vector corresponding to the visual feature sequence and an output task result corresponding to the self-learning label;

decoding the visual encoding feature vector through the decoding network, to obtain an output image report corresponding to the sample medical image;

calculating a total loss function value of the medical image report generation model based on a first loss function value and a third loss function value, the first loss function value being calculated based on the output image report and a target image report corresponding to the sample medical image, and the third loss function value being calculated based on the output task result and a target task result corresponding to the sample medical image; and adjusting a parameter of the medical image report generation model according to the total loss function value.

2. The method according to claim 1, further comprising:

inputting the sample medical image after being rotated by a designated angle into the visual feature extraction network, wherein the target task result includes a real rotation angle of the sample medical image, and the output task result includes a predicted rotation angle of the sample medical image.

3. The method according to claim 1, wherein the input information further comprises a model distillation label, and the model distillation label is processed through the encoding network, to obtain a student output diagnosis result; and the method further comprises:

calculating a fourth loss function value based on the student output diagnosis result and a teacher output diagnosis result corresponding to the sample medical image; and calculating the total loss function value based on the first loss function value, the third loss function value, and the fourth loss function value.

4. The method according to claim 3, further comprising:

inputting the sample medical image into a pre-trained teacher model, the teacher model being configured to recognize a symptom category in the sample medical image; and obtaining the teacher output diagnosis result corresponding to the sample medical image through the teacher model.

5. The method according to claim 3, wherein the calculating the total loss function value based on the first loss function value, the third loss function value, and the fourth loss function value comprises:

performing weighted summation on the first loss function value, the third loss function value, and the fourth loss function value, to obtain the total loss function value.

6. The method according to claim 1, wherein the input information further comprises an image category label, and the image category label is processed through the encoding network, to obtain an output category result corresponding to the image category label; and the method further comprises:

calculating a second loss function value based on the output category result and a target category result corresponding to the sample medical image; and calculating the total loss function value based on the first loss function value, the second loss function value, and the third loss function value.

7. The method according to claim 6, further comprising:

extracting information about a designated field from the target image report corresponding to the sample medical image; and performing semantic recognition on the information about the designated field, to obtain the target category result.

8. The method according to claim 1, wherein the performing visual feature extraction processing on the sample medical image through the visual feature extraction network, to obtain a visual feature sequence of the sample medical image comprises:

performing visual feature extraction processing on the sample medical image through the visual feature extraction network, to obtain the visual feature information about the sample medical image;

dividing the visual feature information into a plurality of visual feature units; and acquiring a feature vector of each of the visual feature units, to obtain the visual feature sequence.

9. A training apparatus for a medical image report generation model, the medical image report generation model comprising a visual feature extraction network, an encoding network, and a decoding network, the apparatus comprising:

a processor and a memory, the memory storing at least one instruction, at least one program, a code set, or an instruction set, the at least one instruction, the at least one program, the code set, or the instruction set being loaded and executed by the processor to implement:

acquiring a sample medical image;

extracting visual feature information of the sample medical image through the visual feature extraction network, to obtain a visual feature sequence of the sample medical image;

concatenating a self-learning label based on the visual feature sequence, to obtain input information about the encoding network;

encoding the input information through the encoding network, to obtain a visual encoding feature vector corresponding to the visual feature sequence and an output task result corresponding to the self-learning label;

decoding the visual encoding feature vector through the decoding network, to obtain an output image report corresponding to the sample medical image;

calculating a total loss function value of the medical image report generation model based on a first loss function value and a third loss function value, the first loss function value being calculated based on the output image report and a target image report corresponding to the sample medical image, and the third loss function value being calculated based on the output task result and a target task result corresponding to the sample medical image; and adjusting a parameter of the medical image report generation model according to the total loss function value.

10. The apparatus according to claim 9, wherein the processor is further configured to perform:

inputting the sample medical image after being rotated by a designated angle into the visual feature extraction network, wherein the target task result includes a real rotation angle of the sample medical image, and the output task result includes a predicted rotation angle of the sample medical image.

11. The apparatus according to claim 9, wherein the input information further comprises a model distillation label, and the model distillation label is processed through the encoding network, to obtain a student output diagnosis result; and the processor is further configured to perform:

calculating a fourth loss function value based on the student output diagnosis result and a teacher output diagnosis result corresponding to the sample medical image; and calculating the total loss function value based on the first loss function value, the third loss function value, and the fourth loss function value.

12. The apparatus according to claim 11, wherein the processor is further configured to perform:

inputting the sample medical image into a pre-trained teacher model, the teacher model being configured to recognize a symptom category in the sample medical image; and obtaining the teacher output diagnosis result corresponding to the sample medical image through the teacher model.

13. The apparatus according to claim 11, wherein the calculating the total loss function value based on the first loss function value, the third loss function value, and the fourth loss function value comprises:

performing weighted summation on the first loss function value, the third loss function value, and the fourth loss function value, to obtain the total loss function value.

14. The apparatus according to claim 9, wherein the input information further comprises an image category label, and the image category label is processed through the encoding network, to obtain an output category result corresponding to the image category label; and the processor is further configured to perform:

calculating a second loss function value based on the output category result and a target category result corresponding to the sample medical image; and calculating the total loss function value based on the first loss function value, the second loss function value, and the third loss function value.

15. A non-transitory computer readable storage medium, storing a computer program for training a medical image report generation model, the medical image report generation model comprising a visual feature extraction network, an encoding network, and a decoding network, the computer program, when being executed by a processor of a computer device, causing the processor to implement:

acquiring a sample medical image;

extracting visual feature information of the sample medical image through the visual feature extraction network, to obtain a visual feature sequence of the sample medical image;

concatenating a self-learning label based on the visual feature sequence, to obtain input information about the encoding network;

encoding the input information through the encoding network, to obtain a visual encoding feature vector corresponding to the visual feature sequence and an output task result corresponding to the self-learning label;

decoding the visual encoding feature vector through the decoding network, to obtain an output image report corresponding to the sample medical image;

calculating a total loss function value of the medical image report generation model based on a first loss function value and a third loss function value, the first loss function value being calculated based on the output image report and a target image report corresponding to the sample medical image, and the third loss function value being calculated based on the output task result and a target task result corresponding to the sample medical image; and adjusting a parameter of the medical image report generation model according to the total loss function value.

16. The storage medium according to claim 15, wherein the computer program further causes the processor to implement:

inputting the sample medical image after being rotated by a designated angle into the visual feature extraction network, wherein the target task result includes a real rotation angle of the sample medical image, and the output task result includes a predicted rotation angle of the sample medical image.

17. The storage medium according to claim 15, wherein the input information further comprises a model distillation label, and the model distillation label is processed through the encoding network, to obtain a student output diagnosis result; and the computer program further causes the processor to implement:

calculating a fourth loss function value based on the student output diagnosis result and a teacher output diagnosis result corresponding to the sample medical image; and calculating the total loss function value based on the first loss function value, the third loss function value, and the fourth loss function value.

18. The storage medium according to claim 17, wherein the computer program further causes the processor to implement:

inputting the sample medical image into a pre-trained teacher model, the teacher model being configured to recognize a symptom category in the sample medical image; and obtaining the teacher output diagnosis result corresponding to the sample medical image through the teacher model.

19. The storage medium according to claim 17, wherein the calculating the total loss function value based on the first loss function value, the third loss function value, and the fourth loss function value comprises:

performing weighted summation on the first loss function value, the third loss function value, and the fourth loss function value, to obtain the total loss function value.

20. The storage medium according to claim 15, wherein the input information further comprises an image category label, and the image category label is processed through the encoding network, to obtain an output category result corresponding to the image category label; and the computer program further causes the processor to implement:

calculating a second loss function value based on the output category result and a target category result corresponding to the sample medical image; and calculating the total loss function value based on the first loss function value, the second loss function value, and the third loss function value.

* * * * *